United States Patent [19]

Krauth

[11] Patent Number: 4,666,866

[45] Date of Patent: May 19, 1987

[54] IMMUNOASSAY FOR ANTIGENS EMPLOYING SUPPORTED BINDER

[76] Inventor: Gary H. Krauth, 3836 W. 9290 South, West Jordon, Utah 84084

[21] Appl. No.: 486,781

[22] Filed: Apr. 19, 1983

[51] Int. Cl.$^4$ ............................................ G01N 33/543
[52] U.S. Cl. .................................... 436/518; 436/528; 436/529; 436/530; 436/531; 436/532; 436/538; 436/541; 436/542; 436/807; 436/808; 436/818; 436/824; 435/7
[58] Field of Search ............... 436/518, 528, 529, 530, 436/531, 532, 538, 541, 542, 807, 808, 818, 824; 435/7

[56] References Cited

U.S. PATENT DOCUMENTS

| | | | |
|---|---|---|---|
| 4,009,005 | 2/1977 | Johnson | 436/527 |
| 4,059,685 | 11/1977 | Johnson | 436/533 |
| 4,067,959 | 1/1978 | Bolz | 436/518 |
| 4,108,976 | 8/1978 | Reese | 436/518 |
| 4,200,625 | 4/1980 | Reese | 436/528 |
| 4,268,494 | 5/1981 | Reese | 436/541 |
| 4,301,139 | 11/1981 | Feingers et al. | 436/541 |
| 4,452,903 | 6/1984 | Lee et al. | 436/808 |
| 4,456,689 | 6/1984 | Witty et al. | 436/824 |

FOREIGN PATENT DOCUMENTS 2304921 10/1976 France ........................... 436/541

Primary Examiner—Christine M. Nucker
Assistant Examiner—Stephen C. Wieder
Attorney, Agent, or Firm—Elliot M. Olstein

[57] ABSTRACT

Assay for a hapten or antigen wherein supported hapten or antigen is used to separate "bound" and "free" fractions. The sensitivity of the assay is increased.

12 Claims, No Drawings

IMMUNOASSAY FOR ANTIGENS EMPLOYING SUPPORTED BINDER

This invention relates to an assay for ligands, and more particularly to an assay for an antigen or hapten.

In an assay for an analyte, which is a hapten or an antigen, by an immunoassay technique, the analyte and tracer compete for a limited number of binding sites on an antibody, with the amount of tracer which is bound by the antibody being inversely proportional to the amount of analyte in the sample. After separating the tracer bound to the antibody, from unbound tracer, at least one of the unbound and free tracer is determined as a measure of the analyte in the sample.

In one type of such assay, generally referred to as a solid phase assay, the antibody is supported on a solid support, whereby tracer bound to the antibody is easily separated from the free tracer which remains in solution.

In another type of assay, after the incubation of analyte, tracer and antibody, the incubated mixture is contacted with solid supported antibody, whereby any tracer which is not bound during the incubation becomes bound to the solid supported antibody. In this manner, tracer bound during the original incubation is separated from tracer which remains in the incubated mixture, and as hereinabove noted, analyte present in the sample may be measured by determining at least one of the amount of bound and free tracer in the incubated mixture. An example of such procedure is described in U.S. Pat. No. 4,108,976, with such patent disclosing an automated procedure by which the solid supported antibody may be reused by subsequently eluting bound material therefrom.

Although the latter procedure is effective for determining an analyte, such procedure necessitates the use of expensive antibodies for separating bound and free tracer present in the incubated mixture.

In a further type of prior art assay, after incubation of analyte, tracer and first antibody, the incubated mixture is contacted with a second antibody supported on a solid support, which second antibody is a binder for the first antibody, whereby any tracer bound to the first antibody is bound to the second antibody through the first antibody to provide a "bound" tracer, and any tracer which is not bound to the first antibody does not bind to the second body to provide a "free" tracer. The amount of "bound" tracer is inversely proportional to the amount of analyte in the sample. This type of assay is often referred to as a "second antibody" assay, and although such assay may be effectively employed, in some cases, there is a need for improved sensitivity.

The present invention is directed to providing an improved assay for an analyte (hapten or antigen) which employs an antigen or hapten on a solid support, as a binder for antibody incubated with the analyte.

More particularly, in accordance with one aspect of the present invention, a mixture of analyte (antigen or hapten), tracer (labeled analyte or appropriate analog thereof), and an antibody specific for the tracer and analyte is incubated, with the antibody having at least two binding sites for the analyte and tracer, and the antibody and tracer being employed in the mixture in amounts at which the tracer does not saturate all binding sites of the antibody.

The term "appropriate analog" as used herein means an analog which binds to the antibody used in the assay.

The term "labeled form of the analyte" means labeled analyte or labeled appropriate analog of the analyte.

The incubated mixture is then contacted with a binder (analyte or appropriate analog thereof) specific for the antibody, whereby any antibody molecule which does not have all of its binding sites occupied, will become bound to the supported binder, and any antibody molecule which has all of its binding sites occupied, and any unbound tracer, will not become bound to the supported binder. In this manner, the amount of antibody which is bound to the supported binder is inversely proportional to the amount of analyte in the sample. Since the antibody has tracer bound thereto, the amount of antibody bound to the binder on the solid support can be determined by measuring the amount of tracer on the fraction bound to the supported binder.

Alternatively, the amount of tracer which is not bound to the binder on the solid support can be determined, and such amount is directly proportional to the amount of analyte in the sample (as the amount of analyte increases, there is an increase in the unbound antibody fraction as a result of saturation of additional binding sites).

As a further alternative, both the amount of tracer bound to the solid supported binder for the antibody and the amount of tracer which is not bound to the solid supported binder for the antibody can be determined as a measure of the amount of analyte present in the mixture which was incubated.

Thus, in accordance with this aspect of the invention, tracer bound to antibody, which is not bound to the supported binder, as well as free tracer (not bound to the antibody), is measured as a "free" fraction (antibody molecules having all of their binding sites saturated with either tracer or analyte), and tracer bound to antibody which is bound to the solid supported binder (antibody having less than all of its binding sites saturated with analyte or tracer) is measured as the "bound" fraction, with the amount of "bound" fraction being inversely proportional to the amount of analyte present in the incubated mixture. The "bound" fraction is comprised of antibody having only one of its sites occupied either by tracer or analyte, whereas the "free" fraction is comprised of unbound tracer and antibody having both sites occupied by analyte and/or tracer.

The binder which is supported on a solid support is either the antigen or hapten which is to be measured as an analyte, or appropriate analog thereof.

Thus, by proceeding with this aspect of the present invention, it is possible to employ antigen or hapten as the solid phase binder in an assay for a hapten or antigen, instead of antibody, as generally used in the prior art.

In accordance with another aspect of the present invention, analyte (antigen or hapten, preferably antigen) is incubated with a tracer which is a labeled antibody for the analyte (the antibody has at least two binding sites for the analyte). After incubation, the mixture is contacted with the analyte or appropriate analog thereof supported on a solid support, whereby labeled antibody molecules having less than all of its binding sites occupied by analyte will become bound to the supported binder and labeled antibody molecules having all of its binding sites occupied by analyte will not bind to the supported binder. As with the assay using labeled analyte or appropriate analog thereof, the amount of antibody bound to the solid support is inversely proportional to the amount of analyte in the same. Thus, the amount of analyte present in the sample can be measured by determining the amount of labeled antibody which is bound and/or not bound by the supported binder.

In this embodiment, as in the previous embodiment, some of the antibody is bound by the supported binder and some of the antibody is not bound by the supported binder. In this embodiment, as in the previous embodiment, hapten or antigen is used as the solid phase binder, in an assay for a hapten or antigen, instead of antibody, as generally used in the prior art.

In accordance with both embodiments, after incubation, the labeled material bound to the supported antigen or hapten (the bound labeled material in one assay is labeled antibody molecules having less than all of its antigenic sites occupied, and in the other assay is tracer bound to the supported antigen or hapten through antibody molecules having less than all of its antigenic sites occupied) is the "bound" fraction, and the labeled material which is not bound to the supported antigen or hapten (labeled antibody molecules having all of its antigenic sites occupied; or unbound tracer and tracer bound to antibody molecules having all of its antigenic sites occupied) is the "free" fraction.

The amount of analyte may be measured by determining the "bound" and/or "free" fraction and by comparing same to a standard curve generated by use of the assay with various known quantities or standard amounts of analyte using techniques generally known in the art.

The present invention may be employed in an assay for a wide variety of antigens and haptens, and preferably for antigens. In general, the antigen which is assayed is characterized by a higher molecular weight, and in particular, such antigens are either polypeptides; in particular, hormones or polypeptide proteins. As representative examples of such antigens, there may be mentioned: hTSH (human thyroid stimulating hormones); HCG; insulin; CEA; ferritin, hepatitis associated antigens A and B, alpha-fetoprotein; growth hormone; FSH, LH, prolactin, gastrin, etc. As representative examples of haptens which may be assayed in accordance with the present invention, there may be mentioned: $T_4$, $T_3$, digoxin, cortisol, estriol, aldosterone, tetosterone, progesterone; various drugs; etc.

The antibody component of the assay is produced by procedures generally known in the art; for example, the antibody can be produced by introducing the antigen into a vertebrate, or if an antibody to a hapten is to be produced, the hapten or appropriate analog thereof bound to protein to produce an immunogen.

The tracer which is employed in the assay, as known in the art, is produced by adding a marker, tag or label in one type of assay to the analyte (ligand) to be assayed or appropriate analog of the analyte; and in the other type of assay to an antibody for the analyte. In accordance with a preferred embodiment, the tracer is produced by using a radioisotope as the marker or label. As representative examples of such radioisotopes, there may be mentioned: the radioisotopes of iodine, tritium, cobalt, and the like, with radioiodine; and in particular $125_I$ being preferred. It is to be understood, however, that the use of other radioisotopes is within the scope of the invention.

Similarly, it is also possible to provide a tracer wherein the analyte or appropriate analog thereof; or the antibody for the analyte is marked or labeled with other than a radioisotope: for example, enzyme labeling; chromogen labeling, including labeling with a fluorescent material; etc. The production of a suitable tracer is deemed to be within the scope of those skilled in the art from the present invention.

The solid supported antigen or hapten which is employed in the present invention, as hereinabove noted, may be either the analyte (ligand) to be assayed, or an appropriate analog thereof. As hereinabove noted, the antigen or hapten (binder) which is supported on the solid support is one which is capable of binding the antibody (labeled or unlabeled) used in the assay. Thus, for example, the supported antigen need not be identical to the analyte nor have the same gross molecular weight. For example, in an assay for human insulin, the supported antigen could be either beef insulin or pork insulin, and in an assay for HCG using antibody to beta-HCG, the supported antigen could be HCG. The selection of a suitable antigen or hapten for use on the solid support is deemed to be within the scope of those skilled in the art from the teachings herein.

The antigen or hapten may be supported on a wide variety of solid material. As known in the art, such materials include suitable polymers, such as polystyrene, polyethylene, polypropylene, polytetrafluoroethylene, polyamides, polyacrylamides, crosslinked agarose, dextran, etc.; glass, bacterial cells; ion exchange resins; cotton, as described in U.S. Pat. No. 4,200,625, and supports of the type described in U.S. Pat. No. 4,059,685, etc. The selection of a suitable support is deemed to be within the scope of those skilled in the art from the teachings herein.

The antigen or hapten may be supported on the solid support by procedures generally known in the art, including adsorption and covalent coupling. In view of the fact that procedures for supporting materials on a solid support are known in the art, no further details in this respect are deemed necessary for a complete understanding of the present invention.

Although the solid support for the antigen or hapten may be in a wide variety of forms, including particles, sheets, tubes, etc., in accordance with a preferred emobdiment, the solid support for the antigen is one which enables the supported antigen to be placed in a flow-through chamber, whereby, the incubated mixture may be caused to flow through a chamber containing the supported antigen. A representative example of such a flow-through chamber is described in U.S. Pat. No. 4,059,685.

In performing the assay, the sample containing or suspected of containing the antigen or hapten to be assayed (analyte) is incubated with the tracer which is either (a) a labeled form of the analyte or appropriate analog thereof or (b) a labeled form of the antibody for the analyte, with the incubation generally being accomplished at a temperature in the order of from 15° C. to 40° C., and for a time sufficient to accomplish the binding.

After the incubation, the mixture is contacted with the supported antigen or hapten, as appropriate, to bind the antibody molecules which do not have both binding sites occupied, with any antibody molecules having both binding sites occupied not being bound by the supported antigen or hapten. In this manner, antibody molecules which are completely saturated are separated from antibody molecules having both of the binding sites occupied.

As hereinabove indicated, by determining the amount of labeled material bound to the supported antigen or hapten and/or the amount of labeled material which is not bound to the supported antigen or hapten, and comparing same to a standard curve, produced by techniques generally known in the art, the amount of analyte present in the sample can be determined.

In accordance with a preferred embodiment, the antibody bound to the supported antigen or hapten is eluted therefrom to permit reuse of the supported antigen or hapten. In this respect, such elution is accomplished by use of a suitable eluting liquid, which elutes the antibody from the supported antigen or hapten, without destroying the binding ability of such supported antigen or hapten.

In accordance with a preferred embodiment, the eluting liquid is one which is at an acidic pH which is no greater than 3.0, and at which the binding ability of the antigen is not destroyed; i.e., the eluting liquid is not made too acidic. In general, the eluting liquid is at a pH of no less than 1.5, and preferably no less than 2.0.

In particular, such eluting liquid is water buffered to a pH as hereinabove described.

The acidic pH may be obtained by the use of any one of a wide variety of acidic buffers. As representative examples of suitable buffers, there may be mentioned: citrates, acetates, glycinates, glutamates, oxalates, tartrates, phosphates, hydrogen chloride, etc., or mixtures thereof. The selection of a suitable buffer is deemed to be within the scope of those skilled in the art from the teachings herein.

The buffer is employed in a concentration which provides the desired eluting, without destroying the binding ability of the supported antigen. In some cases, the eluting ability is enhanced by increasing the salt concentration (ionic strength) of the solution. Such increases in salt concentration may be accomplished by increasing the concentration of the buffer or by the addition of a water soluble salt which does not adversely affect the binder. As representative examples of such salts, there may be mentioned: water soluble salts of an alkali metal or ammonium, such as halides; sulfates, nitrates, phosphates, carbonates, bicarbonates, etc.; water soluble transition metal salts, such as a nitrate, halide, etc., or the like. As hereinabove noted, the total salt concentration, including buffer, is one which provides the desired eluting without destroying the antigenic characteristics of the supported antigen, and in general, the salt concentration does not exceed 4M, and in most cases it does not exceed 2M. In general, the salt concentration is at least 0.01M, when such salt is employed.

It is also to be understood that elution can be accomplished by use of aqueous alcohol at a basic pH; e.g., 75% methanol at pH 13.

Although the present invention is applicable to an assay which does not provide for regeneration of the supported antigen or hapten, the invention has particular applicability to an assay wherein the supported antigen or hapten is regenerated, and is particularly suitable for use in an automated assay. In such an automated assay, the supported antigen or hapten is provided in a flow-through chamber, with the automated apparatus being, for example, of a type disclosed in U.S. Pat. No. 4,009,005.

In one automated assay, the sample containing or suspected of containing the analyte is incubated with tracer (labeled form of the analyte or appropriate ahalog thereof) and antibody for the analyte and tracer, with the resulting mixture being caused to flow through a chamber containing the supported antigen or hapten to separate the antibody molecules having both binding sites occupied by analyte and/or tracer. After the separation, an eluting liquid is passed through the chamber to elute the antibody from the supported antigen, whereby the supported antigen in the chamber may be reused in an assay.

In accordance with one embodiment of such an assay, the tracer is one which has a gamma emitting radioisotope as a label or marker, and the outlet from the chamber is connected to a gamma detector, with the unbound antibody and tracer being initially washed through the chamber and counted, followed by elution of the bound antibody from the supported antigen and counting of the radioisotope which is bound to the antibody eluted from the supported antigen. The percent of the total radioactivity in the fraction which was bound to the supported antigen is inversely proportional to the concentration of analyte in the sample.

In an alternative embodiment, the sample containing or suspected of containing the analyte is incubated with a labeled form of an antibody for the analyte and the incubated mixture is caused to flow through a chamber including the analyte or appropriate analog thereof (hapten or antibody as appropriate) supported on a solid support to separate labeled antibody molecules having a free binding site (bound in the chamber) from labeled antibody molecules having their binding sites completely occupied. The remainder of the assay is as hereinabove described for the assay using labeled analyte.

In accordance with another aspect of the present invention, there is provided a suitable reagent kit or package for accomplishing an assay in accordance with the invention, with such kit or package including as principal components: (a) a tracer for the analyte (labeled form of the analyte or appropriate analog thereof); (b) antibody for the analyte and tracer; and (c) hapten or antigen (analyte or appropriate analog thereof) which is capable of immunobinding the antibody, which antigen or hapten is supported on a solid support.

As an alternative reagent kit or package, the kit or package includes as principal components (a) a labeled form of antibody for the analyte and (b) hapten or antigen (the analyte or appropriate analog thereof) which immunobinds the labeled antibody and which is supported on a solid support.

In accordance with a particularly preferred embodiment, such solid supported antigen or hapten is packaged in a flow-through chamber. In the case where the supported antigen or hapten is to be reused, the reagent kit or package preferably also includes an eluting liquid capable of eluting antibody from the supported antigen or hapten, with the eluting liquid generally being an aqueous eluting liquid of the type hereinabove described. Such components, where applicable, are included in the reagent kit or package in separate containers; for example, vials. The reagent kit or package may also include other components such as standards of the antigen or hapten to be assayed; i.e., antigen or hapten samples having known concentrations of the antigen or hapten to be assayed; buffers; wash liquids; etc.

It is also to be understood that one or more of such materials may be packaged separately and independently from the reagent kit or package and sold as a separate item. Thus, for example, the antigen or hapten supported on a solid support may be separately packaged in a flow-through chamber for sale as a separate item.

Although the assay and kit of the present invention is applicable to a wide variety of assays, Applicant has found that the assay and kit are particularly suitable for an assay for insulin or HCG.

In an assay for insulin, beef or pork insulin is employed as the supported antigen, preferably pork insulin, and is preferably supported on cyanogen bromide activated cotton gauze.

In an assay for HCG, the antigen supported on a solid support is preferably HCG supported on cyanogen bromide activated crosslinked agarose (SEPHAROSE).

The invention will be further described with respect to the following examples; however, the scope of the invention is not to be limited thereby:

EXAMPLE 1

Preparation of Supported Antigen

A known amount of antigen, in a high ionic strength buffer at pH 8.5, is mixed with a fixed amount of cyanogen bromide activated sepharose (Pharmacia) or cotton gauze (Becton Dickinson Immunochemistry) for a period of 2–3 hours at room temperature. The unreacted antigen is removed and the solid support is incubated for one hour at room temperature in ethanolamine to block any excess, unreacted cyanogen bromide groups. The ethanolamine is removed and the solid support is alternatively washed in high ionic strength acidic and alkaline buffers. It is then washed and stored in a physiological buffer prior to use.

EXAMPLE 2

Insulin Assay

In a typical insulin assay performed at room temperature, a 150 µl sample is incubated for 30 minutes with 50 µl (20 nCi) of $^{125}$I-insulin (150 µCi/µg), 80 µl of anti-insulin (1:1000 of guinea pig anti-pork insulin in 50 mM Tris-0.15M Nacl, 0.01% BSA, pH 8.0), and 80 µl of a buffer containing 50 mM Tris-0.15M NaCl, 0.01 BSA, pH 8.0 (adsorption buffer). It is then passed through an 0.5×1.5 cm chamber containing 0.15 mg of pork insulin, coupled to a 6×2.54 cm strip of activated cotton gauze, at 1.0 ml/min for 0.6 minutes. The free fraction (unbound immune complex plus free $^{125}$Insulin) is washed from the column for 1.5 minutes with adsorption buffer at a flow rate of 3 ml/min and counted in the gamma detector equipped with a 1.7 ml flow cell. The bound fraction is eluted from the chamber using a 50 mM glycine buffer at pH 2.0 for 1.3 minutes at a flow rate of 2.5 ml/min. The effluent is mixed with miranol (10 g of an alkyl immidazolinium dicarboxylate salt/liter of water), which flows at 0.5 ml/min for 1.3 minutes and is counted in the gamma detector. The chamber is then re-equilibrated by washing with adsorption buffer for 0.19 minutes at 3.0 ml/min.

Typical performance data for such insulin assay is as follows:

| I. Standard Curve | | |
|---|---|---|
| uU/ml | % BND | Counts |
| 0 | 69.0 | 18245 |
| 5 | 66.3 | 18355 |
| 10 | 63.4 | 18157 |
| 20 | 59.1 | 18102 |
| 40 | 51.4 | 18316 |
| 80 | 40.6 | 18384 |
| 160 | 29.4 | 18727 |
| 320 | 22.5 | 18159 |

| II. Intra-Assay Reproducibility | | | |
|---|---|---|---|
| uU/ml | SD | CV | N |
| Sequential Order | | | |
| 16.0 | 1.8 | 11.3 | 10 |
| 47.0 | 2.0 | 4.2 | 10 |
| 128 | 6.8 | 5.3 | 10 |
| Random Order | | | |
| 16.0 | 1.5 | 8.9 | 10 |
| 50 | 2.9 | 5.7 | 10 |
| 147 | 5.6 | 3.7 | 10 |

$B_o$ = 68.9%
$B_m$ = 12.1%
Intercept = 4.826
Slope = 1.10
C.F. = 0.97
Mean = 18306
CV = 1.08

EXAMPLE 3 hCG Assay

In a typical hCG assay, performed at room temperature, a 150 µl sample is incubated for one hour with 102 µl (20 nCi) of $^{125}$I-hCG (100–150 µCi/µg), 54 µl of anti-hCG-Beta (1:100 of rabbit anti-hCG beta in adsorption buffer) and 306 µl of adsorption buffer. It is then passed through a 0.5×1.5 cm chamber containing 1 mg hCG/ml of activated sepharose at 1.0 ml/min for 0.6 minutes. The free fraction (unbound immune complex plus free $^{125}$I-hCG) is washed from the chamber for 1.75 minutes with adsorption buffer at a flow rate of 1.45 ml/min and counted in the gamma detector equipped with a 1.7 ml flow cell. The bound fraction is eluted from the chamber using a 50 mM glycine buffer at pH 2.0 for 2.32 minutes at a flow rate of 1.45 ml/minute. The chamber is then re-equilibrated by washing with adsorption buffer for 0.33 minutes at 2.35 ml/min and the effluent mixed with miranol (10 g of an alkyl immidazolinium dicarboxylate salt/liter of water) which flows at 3.75 ml/min for 0.08 minutes and then at 8 ml/min for 0.05 minutes.

Typical performance data for an hCG assay is as follows:

| I. Standard Curve | |
|---|---|
| mU/ml | % BND |
| 0 | 44.3 |
| 5 | 41.7 |
| 10 | 40.1 |
| 20 | 35.9 |
| 40 | 29.4 |
| 80 | 21.6 |
| 160 | 14.7 |
| 320 | 10.2 |

| II. Intra-assay Reproducibility | | | |
|---|---|---|---|
| mU/ml | SD | CV | N |
| Sequential Order | | | |
| 26.1 | 1.08 | 4.16 | 10 |
| 52.8 | 1.13 | 2.15 | 10 |

-continued

| 108.3 | 3.11 | 2.88 | 10 |

$B_o = 44.3\%$
$B_m = 5.0\%$
Intercept = 4.60
Slope = 1.14
C.F. = 0.95

In using the assay procedure of Example 3, except that the chamber includes a second antibody (goat antirabbit) supported on activated sepharose, instead of hCG supported on activated sepharose, it was not possible to detect hCG in the range from 0–10 mU/ml. Thus, an assay in accordance with the present invention, has improved sensitivity, as compared to prior art second antibody assay techniques.

EXAMPLE 4

INSULIN ASSAY (LABELED ANTIBODY)

In a typical insulin assay performed at room temperature, a 200 μl sample is incubated for 120 minutes with 100 μl (20 nCi) of $^{125}I$ guinea pig anti-insulin (40 μci/ng and 100 μl of a buffer containing 50 mM Tris-0.15M NaCl, 0.01% BSA, pH 8.0 (adsorption buffer). It is then passed through an 0.5×1.5 cm chamber containing 0.25 mg of pork insulin, coupled to sepharose. The free fraction (unbound immune complex) is washed from the column with adsorption buffer and counted in the gamma detector equipped with a 1.7 ml flow cell. The bound fraction is eluted from the chamber using a 50 mM glycine buffer at pH 2.0. The effluent is mixed with miranol (10 g of an alkyl immidazolinium dicarboxylate salt/liter of water), and is counted in the gamma detector. The chamber is then re-equilibrated by washing with adsorption buffer.

Typical performance data for such insulin assay is as follows:

| I. Standard Curve | |
| --- | --- |
| uU/ml | % BND |
| 0 | 80% |
| 1 | 77% |
| 2.5 | 72% |
| 5.0 | 68% |
| 10.0 | 62% |
| 25.0 | 57% |
| 50.0 | 54% |
| 100.0 | 50% |

The present invention is particularly advantageous in that it permits the use of a solid supported antigen in place of solid supported antibody. The use of solid supported antigen not only provides a less costly procedure, but in addition, there is an increase in the sensitivity of the assay.

Numerous modifications and variations of the present invention are possible in light of the above teachings and, therefore, within the scope of the appended claims, the invention may be practiced otherwise than as particularly described.

What is claimed is:

1. An assay for an analyte selected from the group consisting of haptens and antigens, comprising:
incubating the analyte with a tracer comprising a labeled form of the analyte, and with an antibody for the tracer and analyte to provide an incubated mixture, said antibody being present in an amount to provide in the incubated mixture a first portion of antibody molecules, including tracer bound thereto having less than all of the binding sites occupied and a second portion of antibody molecules including tracer bound thereto having all of the binding sites occupied; contacting the incubated mixture with a binder for the antibody supported on a solid support, said binder being selected from the group consisting of antigens and haptens whereby said first portion of antibody molecules is bound to the supported binder and the second portion of antibody molecules is not bound to the supported binder; separating bound material from unbound material; and determining at least one of the amount of tracer in the bound material and the amount of tracer in the unbound material as a measure of analyte.

2. The process of claim 1 wherein the analyte is an antigen.

3. The process of claim 2 wherein the supported binder is supported in a flowthrough chamber.

4. The process of claim 3 wherein the labeled form of the analyte is labeled with a radioisotope.

5. The process of claim 4 wherein the analyte is insulin.

6. The process of claim 5 wherein the supported binder is insulin supported on activated cotton.

7. The process of claim 4 wherein the analyte is hCG.

8. The process of claim 7 wherein the supported binder is hCG supported on activated crosslinked agarose.

9. The process of claim 4 and further comprising eluting bound antibody from the supported binder for reuse of the supported binder in an assay.

10. The process of claim 9 wherein the eluting is effected with an aqueous eluting liquid buffered to a pH of no greater than 3 and no less than 1.5.

11. A reagent kit for the assay of an analyte selected from the group consisting of haptens and antigens, comprising:
in a reagent package antibody for the analyte, a tracer comprising a labeled form of the analyte; and
a binder for the antibody supported on a solid support, said binder being selected from the group consisting of antigens and haptens.

12. The kit of claim 11 wherein the binder supported on the solid support is in a flowthrough chamber.

* * * * *